(12) United States Patent
Wunz et al.

(10) Patent No.: US 11,045,742 B2
(45) Date of Patent: Jun. 29, 2021

(54) TEMPERATURE CONTROLLED PURIFICATION MODULE AND METHOD

(71) Applicant: Jaxon Technologies, LLC, State College, PA (US)

(72) Inventors: Chris Wunz, State College, PA (US); Roshan Jeet Jee Jachuck, Delray Beach, FL (US); Sam Gorton, Enosburg Falls, VT (US)

(73) Assignee: Jaxon Technologies, LLC, State College, PA (US)

( * ) Notice: Subject to any disclaimer, the term of this patent is extended or adjusted under 35 U.S.C. 154(b) by 0 days.

(21) Appl. No.: 16/692,058

(22) Filed: Nov. 22, 2019

(65) Prior Publication Data

US 2021/0154591 A1 May 27, 2021

(51) Int. Cl.
| | |
|---|---|
| *B01D 1/08* | (2006.01) |
| *B01D 1/00* | (2006.01) |
| *C07C 37/76* | (2006.01) |
| *B01D 5/00* | (2006.01) |
| *C07D 311/80* | (2006.01) |
| *B01D 3/42* | (2006.01) |

(52) U.S. Cl.
CPC ............. *B01D 1/08* (2013.01); *B01D 1/0047* (2013.01); *B01D 3/42* (2013.01); *B01D 5/006* (2013.01); *C07C 37/76* (2013.01); *C07D 311/80* (2013.01)

(58) Field of Classification Search
CPC .......... B01D 1/08; B01D 1/0047; B01D 3/42; B01D 5/006; C07C 37/76; C07C 311/80
See application file for complete search history.

(56) References Cited

U.S. PATENT DOCUMENTS

| | | | | | |
|---|---|---|---|---|---|
| 2,427,142 | A | * | 9/1947 | Hornbacher | ......... G01N 25/145 165/73 |
| 2,520,494 | A | * | 8/1950 | Dalin | ..................... B01D 3/166 219/506 |
| 3,240,682 | A | * | 3/1966 | Gordon | .................. G01N 25/14 202/158 |
| 3,395,083 | A | * | 7/1968 | Gilmont | .................. B01L 3/569 202/83 |
| 3,607,662 | A | * | 9/1971 | Glover | ................. B01D 5/0045 202/160 |
| 3,907,683 | A | * | 9/1975 | Gilmont | ................... B01D 3/00 202/177 |

(Continued)

*Primary Examiner* — Jonathan Miller
(74) *Attorney, Agent, or Firm* — Burr & Forman LLP

(57) ABSTRACT

A purification module configured to separate and purify a liquid solution is provided. The purification module may include a vessel configured to receive a predetermined amount of a liquid solution. The purification module may also include a heating apparatus configured to apply heat to the vessel at a temperature of a first boiling point, and a column apparatus configured to separate the liquid solution into a first liquid and a second liquid and purify the first liquid and the second liquid to a determined purity level. The column apparatus may include a first heating chamber, a second heating chamber, and a distillation chamber. The distillation chamber may be located between the first heating chamber and the second heating chamber. The first heating chamber and second heating chamber may be configured to receive a heat transfer liquid to apply heat to the distillation chamber at the temperature of the first boiling point.

19 Claims, 6 Drawing Sheets

(56) References Cited

U.S. PATENT DOCUMENTS

| | | | | |
|---|---|---|---|---|
| 4,724,048 A | * | 2/1988 | Helmich | B01D 3/02 |
| | | | | 159/23 |
| 5,033,541 A | * | 7/1991 | D'Silva | B01D 5/0009 |
| | | | | 165/155 |
| 5,076,349 A | * | 12/1991 | Kadono | B01D 5/0042 |
| | | | | 165/111 |
| 5,164,049 A | * | 11/1992 | Clark | B01D 1/02 |
| | | | | 134/12 |
| 5,698,158 A | | 12/1997 | Lam et al. | |
| 5,885,313 A | * | 3/1999 | Okamoto | B01D 3/085 |
| | | | | 55/315.2 |
| 10,029,188 B2 | * | 7/2018 | Kremerman | B01D 3/085 |
| 2008/0128261 A1 | * | 6/2008 | Balass | B01D 5/006 |
| | | | | 202/176 |
| 2008/0183427 A1 | * | 7/2008 | Miller | G05B 23/024 |
| | | | | 702/183 |

\* cited by examiner

US 11,045,742 B2

TEMPERATURE CONTROLLED PURIFICATION MODULE AND METHOD

TECHNICAL FIELD

Example embodiments generally relate to separation of a liquid solution into individual liquid components and purifying the individual liquid components to a desired purity level.

BACKGROUND

Separation and purification of liquids having similar or close boiling points has generally been accomplished via short path distillation systems such as wiped or thin film evaporators, specifically in relation to the separation of tetrahydrocannabinol (THC) and cannabidiol (CBD) from a crude *cannabis* oil extract. Short-path distillation systems, however, are difficult to maintain and operate and are only a single stage process. Specifically, once the vapors of the liquids being separated and purified are generated and condensed, no further purification of the liquids can be accomplished. Thus, the short-path distillation system allows only for a single-phase separation and purification of the liquids.

BRIEF SUMMARY OF SOME EXAMPLES

An example embodiment may provide for a purification module configured to separate and purify a liquid solution. The purification module may include a vessel configured to receive a predetermined amount of a liquid solution. The liquid solution may include a first liquid having a first boiling point and a second liquid having a second boiling point, and the first boiling point may be lower than the second boiling point. The purification module may also include a heating apparatus configured to apply heat to the vessel at a temperature of the first boiling point, and a column apparatus configured to separate the liquid solution into the first liquid and the second liquid and purify the first liquid and the second liquid to a determined purity level. The column apparatus may include a first heating chamber, a second heating chamber, and a distillation chamber. The distillation chamber may be located between the first heating chamber and the second heating chamber. The first heating chamber and second heating chamber may be configured to receive a heat transfer liquid to apply heat to the distillation chamber at the temperature of the first boiling point in order to enable separation and purification of the first liquid and the second liquid in the distillation chamber.

A further example embodiment may provide for a column apparatus configured to separate and purify a liquid solution. The liquid solution may include a first liquid having a first boiling point and a second liquid having a second boiling point. The column apparatus may include a first heating chamber, a second heating chamber, and a distillation chamber. The distillation chamber may be located between the first heating chamber and the second heating chamber. The first heating chamber and second heating chamber may be configured to receive a heat transfer liquid to apply heat to the distillation chamber at the temperature of the first boiling point in order to enable separation and purification of the first liquid and the second liquid in the distillation chamber. The first boiling point may be lower than the second boiling point.

An even further example embodiment may provide for a method of separating and purifying a liquid solution. The liquid solution may include a first liquid having a first boiling point and a second liquid having a second boiling point. The first boiling point may be lower than the second boiling point. The method may include providing an amount of the liquid solution in a vessel and applying heat, via a heating apparatus, to the vessel at a temperature of the first boiling point. The method may also include applying heat, via heat transfer fluid in a first heating chamber and a second heating chamber, at the temperature of the first boiling point as vapor generated from the liquid solution travels up a distillation chamber, and collecting and cooling the vapor of the first liquid until a predetermined purity level is reached.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
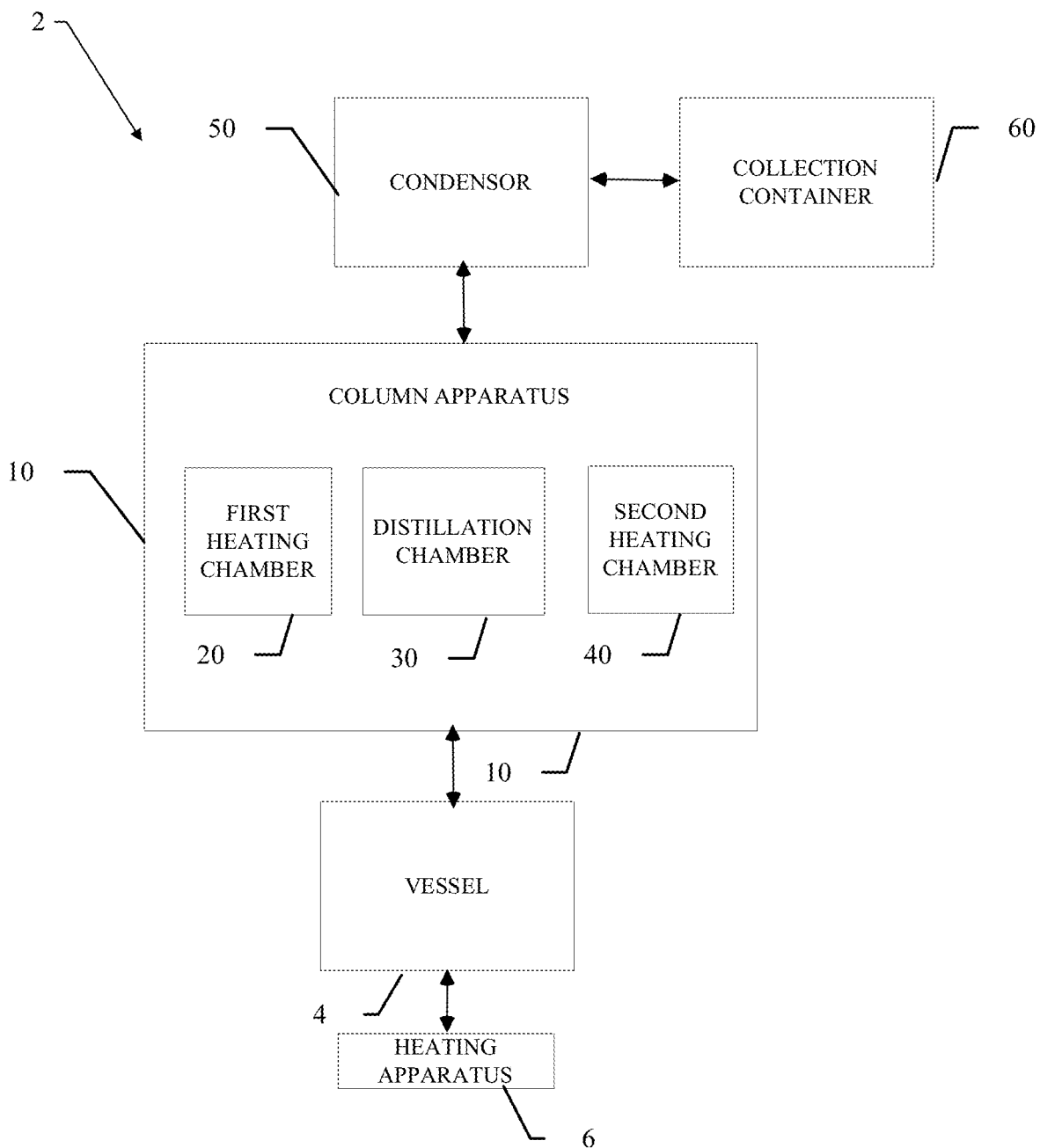
FIG. 1 illustrates a block diagram of a purification module according to an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. Furthermore, as used herein, the term "or" is to be interpreted as a logical operator that results in true whenever one or more of its operands are true.

Some example embodiments disclosed herein may allow for the separation of a liquid solution into individual components and purification of those individual components. In this regard, the separation and purification of the liquid solution as described herein may be a temperature-controlled, multi-stage process that allows for the separation and purification of the liquid solution into individual liquid components. The temperature-controlled, multi-stage process allows for the purification of the individual liquid components until a desired purity of the individual liquid components is reached.

Figure 2:
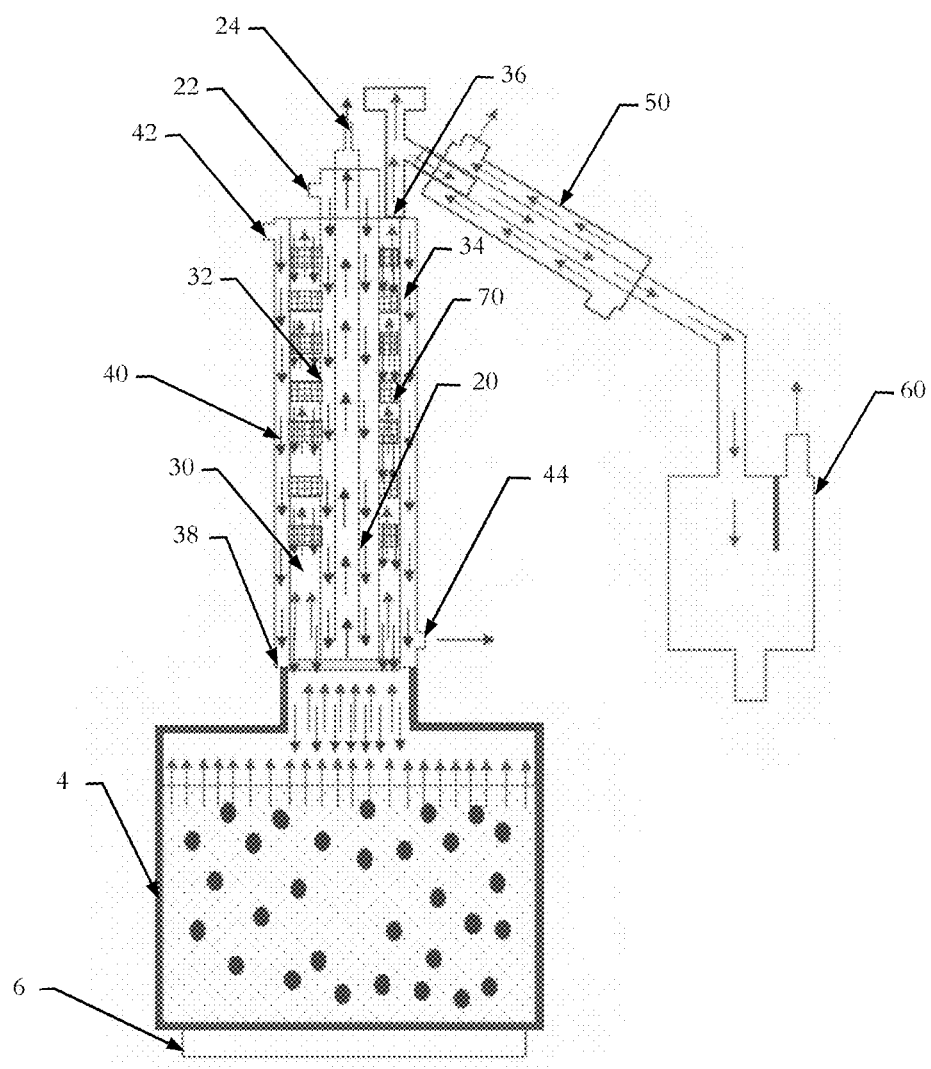
FIG. 2 illustrates a diagram of a purification module according to an example embodiment.

FIGS. 1 and 2 illustrate a purification module 2 according to an example embodiment. The purification module 2 described herein is configured to separate and purify liquid components in a liquid solution. These individual liquid components may be a first liquid and a second liquid, and each of the first liquid and the second liquid may have similar boiling points, as further discussed below. In this regard, one example embodiment may relate to the separation of THC and CBD from a crude *cannabis* solution. The *cannabis* solution may be produced by methods or processes known to one of ordinary skill in the art. While the purification module 2 may be discussed in relation to the separation and purification of THC and CBD from a crude *cannabis* oil, it should be understood that the purification module 2 may be used for the separation and purification of any liquid solutions having component liquids with close or similar boiling points.

As shown in FIGS. 1 and 2, the purification module 2 may include a vessel 4 for receiving a liquid solution having a first liquid and a second liquid. The vessel 4 may be configured to receive a predetermined amount of the liquid solution for separation and purification. However, in accordance with other example embodiments, the vessel 4 may be configured to receive a continuous feed of the liquid solution. Accordingly, the purification module 2 may be configured to operate either in a batch mode or a continuous mode. In this regard, in the batch mode, the vessel 4 of the purification module 2 may receive a predetermined amount of liquid solution, and the purification module may operate until a desired or defined purity is reached. In the continuous mode, the vessel 4 of the purification module 2 may receive a continuous supply of liquid solution, and the purification module 2 may operate until a desired or defined purity is reached. Furthermore, the vessel 4 may be any vessel, kettle, or container known in the art that is configured to be heated to a predefined temperature via a heating apparatus 6 of the purification module 2.

The liquid solution received in the vessel 4 may be a mixture of a plurality of liquids. In accordance with some example embodiments, the liquid solution may include a first liquid and a second liquid. In this regard, the liquid solution may be a crude *cannabis* oil including THC and CBD liquid components. However, in some example embodiments, the liquid solution may include more than two different liquid components (e.g., the first liquid, the second liquid, and a third liquid). At least some of the separate liquids in the liquid solution (e.g., the first liquid and the second liquid) may have close or similar boiling points. In this regard, the boiling points may be within 1-30 degrees Celsius of one another. The boiling points of each of the liquids in the liquid solution may be within at most 30, 25, 20, 15, 10, or 9 degrees Celsius or at least 8, 7, 6, 5, 4, 3, 2, or 1 degrees Celsius (e.g., about 5-30 or 1-10, etc.) of one another. For example, the first liquid may have a boiling point of 85° C., and the second liquid may have a boiling point of 90° C.

Furthermore, the vessel 4 may be operably coupled to a column apparatus 10. The column apparatus 10 may be configured to separate the first liquid from the second liquid and purify either of or both of the first liquid and second liquid to a desired or defined level. As shown in FIGS. 1 and 2, the column apparatus 10 may include a first heating chamber 20, a second heating chamber 40, and a distillation chamber 30. The distillation chamber 30 may be disposed between the first heating chamber 20 and the second heating chamber 40, and each of the first heating chamber 20 and the second heating chamber 40 may be configured to apply heat to the distillation chamber 30. In other words, the first heating chamber 20 may be disposed at or proximate a center axis of the distillation chamber 30, and the second heating chamber 40 may be surrounded by an exterior circumference of the distillation chamber 30.

Figure 3:
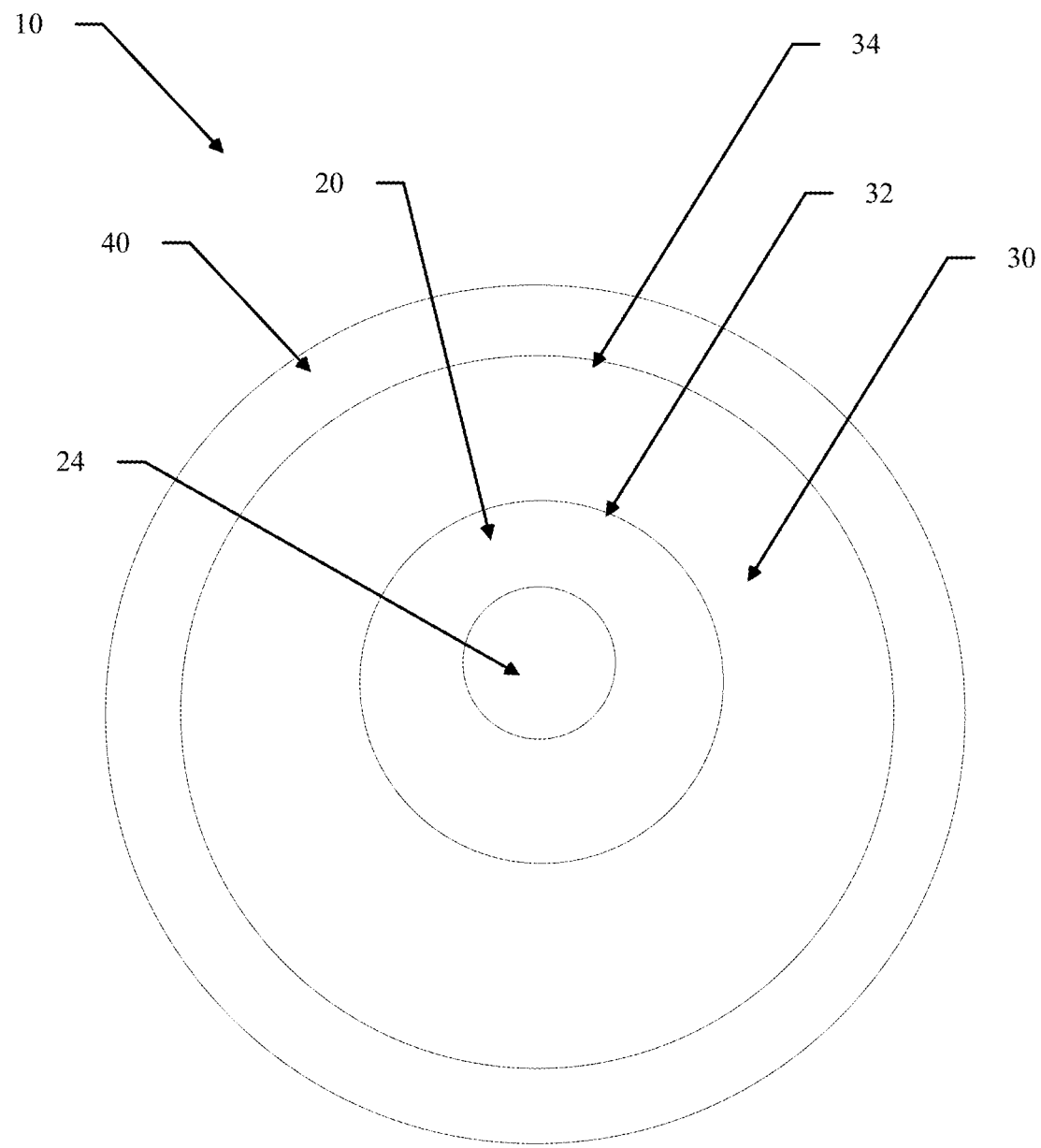
FIG. 3 illustrates a cross-section of a column apparatus of a purification module according to an example embodiment.

FIG. 3 illustrates a cross section of the column apparatus 10. As shown in FIGS. 2 and 3, the distillation chamber 30 may include an inner wall 32 and an outer wall 34 defining a longitudinal length of the distillation chamber 30. The inner wall 32 may also define a wall of the first heating chamber 20 and the outer wall 34 may define a wall of the second heating chamber 40. Accordingly, each of the inner wall 32 and the outer wall 34 of the distillation chamber 30 may be surrounded by a respective one of the first heating chamber 20 and the second heating chamber 40. Furthermore, each of the first heating chamber 20 and the second heating chamber 40 may have a fluid inlet 22, 42 and a fluid outlet 24, 44. A heat transfer fluid may enter the fluid inlet 22, 42 of each of the first and the second heating chamber 20, 40 at a predefined or controllable flow rate and circulate through the first and the second heating chamber 20, 40 and exit via the respective fluid outlet 24, 44 in order to heat the inner and outer walls 32, 34 of the distillation chamber 30. The heat transfer fluid may be water or any other liquid that is configured to transfer heat. While example embodiments described herein describe heating chambers configured to heat a liquid solution, other example embodiments may provide for a chamber that is configured to cool the liquid solution in order to achieve the desired purity level described herein.

As mentioned above, the heating apparatus 6 may be configured to apply heat to the vessel 4 at a predetermined or controllable temperature. The heating apparatus 6 may be a reboiler or any other heating apparatus known in the art configured to apply heat to the vessel 4. The predetermined temperature may be the lower boiling point of the first and second liquids. In this regard, if the first liquid has a boiling point of 85° C. and the second liquid has a boiling point of 90° C., the heating apparatus 6 may be configured to heat the vessel 4 at 85° C. As the heating apparatus 6 applies heat to the vessel 4, the first liquid having the lower boiling point (e.g., 85° C.) may begin to vaporize and rise up through distillation chamber 40. While the first liquid will begin to vaporize first, the second liquid may also begin to vaporize as well and travel up the longitudinal length of the distillation chamber 40 toward a condenser 50 operably coupled to the distillation chamber 30. The condenser 50 may be operably coupled to a first end 36 of the distillation chamber 30 opposite from a second end 38 of the distillation chamber 30 to which the vessel 4 is operably coupled.

Furthermore, the heat transfer fluid may enter each of the first and second heating chambers 20, 40 via the respective fluid transfer inlets 22, 42 upon the heating apparatus 6 heating the liquid solution in the vessel 4. The heat transfer fluid may also have a predefined or controllable temperature based on the boiling point of the liquid having the lower boiling point. In distillation chambers known in the art, the vapor starts to cool as the vapor rises through the distillation chamber. However, the heat transfer fluid circulating in the first heating chamber 20 and the second heating chamber 40 discussed herein serves to heat the inner and outer walls 32, 34 of the distillation chamber 30. The heat being applied to the inner and outer walls 32, 34 of the distillation chamber 30 facilitates the continuing vaporizing of the first liquid as the vapor of the first liquid travels up the longitudinal length of the distillation chamber 30. In this regard, if the first liquid contacts the inner and outer walls 32, 34 of the distillation chamber 30, the vapor of the first liquid will continue to boil as the heat transfer fluid in the first and second heating chambers 20, 40 is configured to heat the inner and outer walls 32, 34 of the distillation chamber to the boiling point of the first liquid (i.e., the liquid having the lower boiling point). However, when the vapor of the second liquid, which has a higher boiling point than the first liquid, comes into contact with the inner and outer walls 32, 34 of the distillation chamber 30, the vapor of the second liquid may condense and fall back down the inner and outer walls 32, 34 of the distillation chamber into the vessel 4 due to having a boiling point higher than the temperature of the inner and outer walls 32, 34. Accordingly, as the inner and outer walls 32, 34 of the distillation chamber 30 are being heated to the boiling point of the first liquid, the purification of the first liquid is enhanced, as the vapor of the first liquid will continue to travel up the longitudinal length of the distillation chamber to the condenser 50. Furthermore, in some example embodiments, the inner and outer walls 32,34 of the distillation chamber 30 may include or defines grooves. The grooves may be configured to increase residence time of the vapor and gas-liquid mass contact time and also increase heat transfer surface area thereby facilitating the condensation of the second liquid while enabling the vapor of the first liquid to travel up the longitudinal length of the distillation chamber 30.

In some cases, the distillation chamber 30 may also include a plurality of condensation structures 70 disposed in an interior of the distillation chamber 30. In this regard, the plurality of condensation structures 70 may be disposed at predetermined distances along the longitudinal length of the distillation chamber 30 from the second end 38 of the distillation chamber 30. In this regard, each of the condensation structures 70 may be disposed at different distances from the second end 38 of the distillation chamber 30. Furthermore, each of the plurality of condensation structures 70 may extend between and be in contact with at least one of the inner and outer walls 32, 34 of the distillation chamber 30 or, in some cases, both the inner and outer walls 32,34. Similar to the inner and outer walls 32, 34 of the distillation chamber 30, the condensation structures 70 may also be heated to the temperature of the boiling point of the first liquid by, for example, the heat transfer liquid flowing through the first and the second heating chamber 20, 40. As the vapor of the first liquid and the second liquid rises vertically up through the distillation chamber 30, the vapor of the first liquid and the second liquid may come into contact with the condensation structure 70. However, due to the temperature of the condensation structure 70 being at the boiling point of the first liquid, the vapor of the first liquid will continue to boil and therefore continue to rise up through the distillation chamber 30. A surface area of the condensation structures 70 allows for at least some of the vapor of the second liquid to condense on the condensation structure 70. In this regard, not all of the vapor of the second liquid may come in to contact with and condense upon contact with a first condensation structure 70 encountered. Rather, the vapor of the second liquid may condense in stages as the vapor of the second length is traveling up the longitudinal length of the distillation chamber 30 either on another condensation structure 70 or the inner or outer wall 32,34 of the distillation chamber. In this regard, the plurality of condensation structures 70 allow for a multi-stage condensation of the vapor of the second liquid, and thus the purity level of the first liquid may increase as the liquid solution travels up the longitudinal length of the distillation chamber 30. In this regard, each condensation structure 70 creates a thin film distribution and provides an enhanced surface area to allow multiple stages in which the vapor of the second liquid can condense and enhance the purification of the first liquid.

To enable the vapor to pass through the condensation structure 70, the condensation structure 70 may have a slotted structure. In this regard, each of the condensation structures 70 may have a slotted tray or a mesh structure to enable vapor to continue to travel up the longitudinal length of the distillation chamber 30. In cases, where the condensation structure 70 is a mesh structure, each of the condensation structures 70 may have a different porosity. In this regard, the porosity of each condensation structure 70 may increase moving from the second end 38 of the distillation chamber 30 toward the first end 36 of the distillation chamber 30.

Furthermore, each of the condensation structures 70 may be formed of metal or conductive material configured to conduct heat or obtained a desired heat transfer level. In this regard, the metal forming the condensation structure 70 may be configured to be heated by the heat transfer liquid in the first and the second heating chamber 20, 40. Additionally, the metal forming the condensation structure 70 may be resistant to any corrosion that could potentially be caused by the vapor of the first liquid or the second liquid. Furthermore, the metal forming the condensation structures 70 may be coated with a catalyst to increase the heat transfer level.

In some cases, rather than the condensation structures 70 being disposed at predetermined distances from the second end 38 of the distillation chamber 30, the condensation structure 70 may be a mesh packing disposed substantially along the longitudinal length of the distillation chamber 30. In this regard, mesh packing may be a collection of woven or non-woven metal fibers and be used to substantially fill the distillation chamber in a manner that allows vapor to pass through the mesh packing while also providing surfaces on which the vapor of the second liquid may condense. In other example embodiments, a plurality of mesh packings may be included that extend and are disposed at predetermined intervals around the circumference of the distillation chamber 30 substantially from the second end of the distillation chamber 38 to the first end 36 of the distillation chamber 30.

As described above, as the vapor of the first liquid rises, the vapor will contact the inner and outer walls 32, 34 and the condensation structures 70. Because the inner and outer walls 32, 34 and the condensation structures 70 are heated to the boiling point of the first liquid, the vapor of the first liquid will continue to boil and continue rising up the distillation chamber 30. However, as the vapor of the second liquid travels up the longitudinal length of the distillation chamber 30, the vapor will condense at multiple stages on the inner and outer walls 32, 34 and the condensation structures 70 due to the temperature of the inner and outer walls 32, 34 and the condensation structures 70 being lower than the boiling point of the second liquid thereby gradually purifying the first liquid as the liquid solution travels up the longitudinal length of the distillation chamber 30. In this regard, because the heating of the inner and outer walls 32, 34 and the condensation structures 70 to the boiling point of the first liquid enhances the purification of the first liquid, the column apparatus 10 is configured to maintain a uniform temperature of the boiling point of the first liquid.

To maintain the temperature of the column apparatus 10, a rate of heat transfer liquid flowing through each of the first heating chamber 20 and the second heating chamber 40 may be controlled. In this regard, according to some example embodiments, the temperature of the heat transfer liquid does not need to be constantly adjusted to maintain a uniform temperature. Rather, if the temperature of the column apparatus 10 begins to fall below the boiling point of the first liquid, the flow rate of the heat transfer liquid flowing through the first heating chamber 20 and the second heating chamber 40 may be increased to increase the temperature. If the temperature of the column apparatus 10 begins to rise above the boiling point of the first liquid, the flow rate of heat transfer liquid flowing through the first heating chamber 20 and the second heating chamber 40 may be decreased. It should be understood that the flow rate of the heat transfer liquid circulating through each of the first heating chamber 20 and the second heating chamber 40 may be adjusted individually to achieve the uniform temperature within the distillation chamber 30 along the longitudinal length of the distillation chamber 30.

The vapor reaching the first end 36 of the distillation chamber 30 may then enter the condenser 50. The condenser 50 is configured to cool or chill the vapor back into a liquid, and then the condensed liquid may be stored in the collection container 60. Any vapor remaining in the distillation chamber 30 or vessel 4 may continue being processed until a desired purity of either the first liquid, the second liquid, or both is reached.

In example embodiments where the liquid solution is a crude *cannabis* oil extract, the heating of the vessel 4 may cause the CBD and THC liquid components to vaporize. THC has a boiling point of 157° C. and CBD has a boiling point 160-180° C. Because THC has the lower boiling point, the heating apparatus 6 will be configured to heat the vessel 4 to 157° C. THC vapor will begin rising up the distillation chamber 30 first and may eventually be mixed with CBD vapor. The heat transfer fluid will also be configured to apply heat to inner and outer walls 32, 34 of the distillation chamber 30 and the condensation structures 70 to a temperature of 157° C. in order to enhance the purification of the THC. The CBD may condense on the inner and outer walls 32, 34 and the condensation structures 70 as the CBD vapor travels up the distillation chamber 30 at multiple stages as discussed above and may flow back into the vessel 4. However, due to the temperature of the inner and outer walls 32, 34 and the condensation structures 70, the THC vapor will continue to boil and rise up into the condenser 50 to be cooled back into a liquid. The THC liquid may then be transferred to the collection container 60. The purification module 2 may continue to operate until a desired purity of either the CBD in the vessel 4 or the THC in the collection container 60 is reached.

Figure 4:
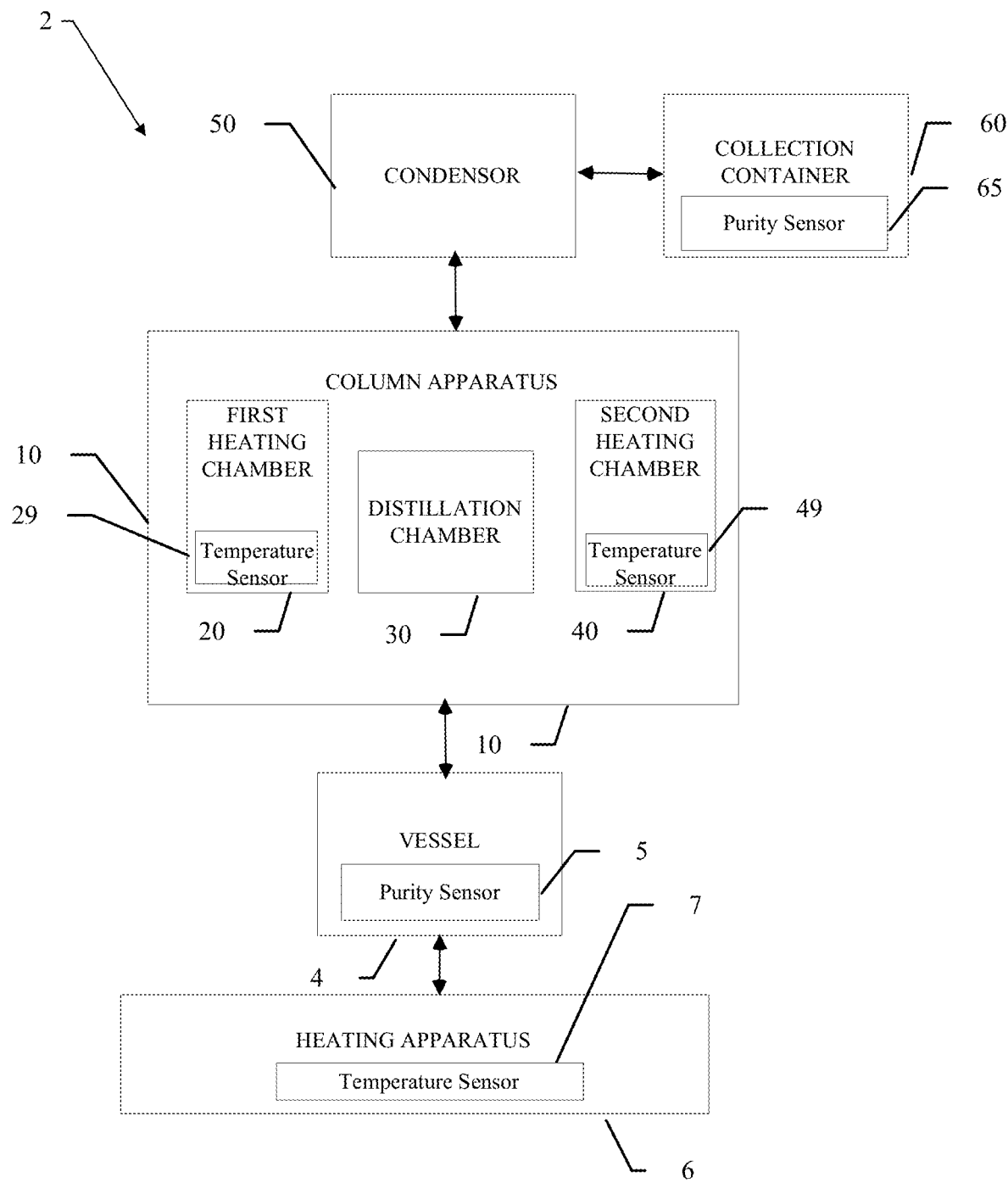
FIG. 4 illustrates a block diagram of a purification module according to a further example embodiment.

FIG. 4 illustrates the purification module 2 according to a further example embodiment. In this regard, the purification module 2 may include various sensors to monitor the operating parameters of the purification module 2. In this regard, to monitor the temperature of the heat transfer fluid circulating in each of the first heating chamber 20 and the second heating chamber 40, each of the first heating chamber 20 and the second heating chamber 40 may include respective temperature sensors 29, 49. In this regard, the temperature sensors 29, 49 may facilitate the monitoring the temperature of the heat transfer fluid to maintain a uniform temperature, as discussed above. As further shown in FIG. 4, to monitor the purity levels, one of or both of the vessel 4 and the collection container 60 may include a purity sensor 5, 65. The purity sensors 5, 65 may be configured to detect the purity level of the liquid in the respective vessel 4 or collection container 65. The purity sensors 5, 65 facilitate the monitoring of the purity levels of the liquids contained in the vessel 4 and the collection container 60. Additionally, the heating apparatus 6 may include a temperature sensor 7 that is configured to facilitate the monitoring of the temperature being applied by the heating apparatus 6 to the vessel 4.

Figure 5:
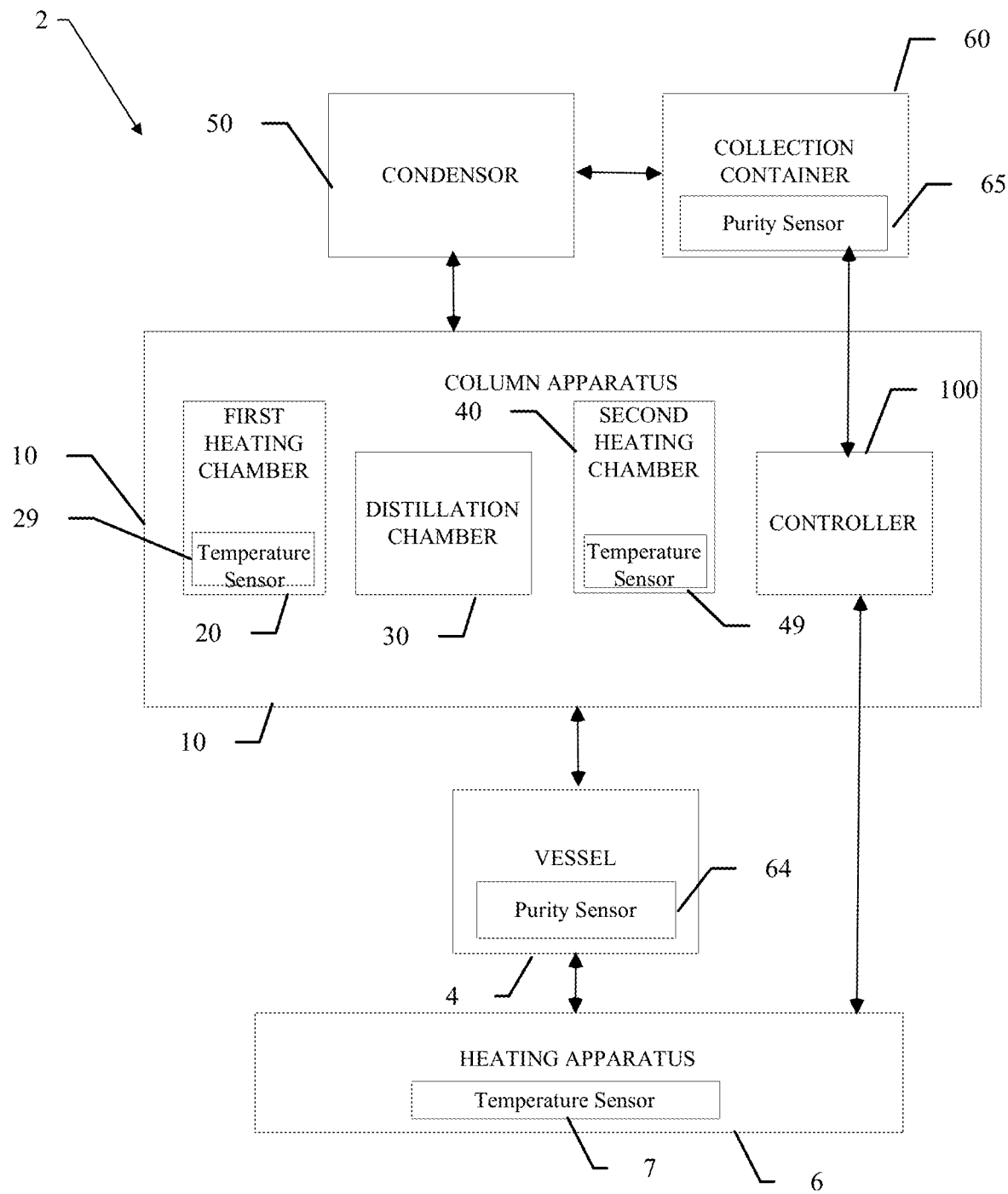
FIG. 5 illustrates a block diagram of a purification module according to an even further example embodiment.

FIG. 5 illustrates the purification module according to an even further example embodiment. In this regard, the purification module 2 may include a controller 100 configured to monitor operational parameters under which the purification module is operating. In other words, rather than an operator monitoring the conditions under which the purification module 2 are operating, the controller 100 may be configured to monitor the operating conditions of the purification module 2 based on initial operator inputs. In other words, the controller 100 may be configured to monitor any of the temperature of the vessel 4, the temperature of the heat transfer fluid in either or both of the first heating chamber 20 and the second heating chamber 40, and the purity levels of either or both of the liquid in the vessel 4 and the collection container 60. The controller 100 may be configured to receive data from any of the temperature sensor 7 of the heating apparatus 6, the purity sensors 5, 65 of the vessel 4 and the collection container 60, and the temperature sensors 29, 49 of the first heating chamber 20 and the second heating chamber 40 in order to control the separation and purification of the liquid solution.

In some cases, the purification module 2 may include an interface panel (not shown) that allows for the operator of the purification module 2 to program the desired or defined parameters of the separation and purification process. Accordingly, the interface panel may be a graphical user interface (GUI) that is easily programmed by the operator. In an example embodiment, the interface panel may include a touch screen display capable of providing visual indications to the operator and further capable of receiving touch inputs from the operator. In certain example embodiments, the interface panel may include a simple interface of buttons, lights, dials and/or the like. In further examples, the operator may remotely control the interface panel from a mobile electronic device including, but not limited to, a smartphone, a tablet, a laptop and/or the like.

The controller 100 may include processing circuitry (e.g., a processor and memory) configured to store instructions and execute the same in order to control the separation and purification process. Thus, for example, the controller 100 may be understood to execute one or more algorithms defining the separation and purification process for the purification module 2. The controller 100 may be configured to receive inputs descriptive of the boiling points of the individual components of the liquid solution (e.g., the boiling point of the first liquid and the second liquid), the volume of liquid solution to be received in the vessel (e.g., continuous feed or predetermined volume), and the desired purity of either or both of the first liquid or the second liquid in order to provide instructions or controls to the purification module 2 in order control the separation and purification process.

The controller 100 may be configured to execute various programs in order to ensure that the programmed purity levels are achieved. Accordingly, the controller 40 may execute programs to ensure the heating apparatus 6 and the heat transfer fluid of each the first heating chamber 20 and the second heating chamber 40 are maintained at the proper temperature (e.g., the lower boiling point between the first liquid and the second liquid) to achieve the programmed purity level. In this regard, the controller 100 may be configured to direct the heating apparatus 6 to apply a predetermined temperature equivalent to the lower boiling point of the first liquid or the second liquid. The controller 100 also may direct a flow rate of the heat transfer fluid in each of the first heating chamber 20 and the second chamber 40 to facilitate the separate and purification of liquids in the liquid solution. Accordingly, the controller 100 may be configured to monitor the data received from the temperature sensors 6, 29, and 49 in order to ensure that the proper temperature of the vessel 4 and the column apparatus 10 is maintained. Furthermore, the controller 100 may also be configured to monitor the data received from the purity sensors 5, 65 in order to ensure the programmed purity level(s) are reached. Accordingly, the controller 100 may control the operational parameters of the purification module 2 discussed herein in order to ensure the programmed purity levels are achieved.

Figure 6:
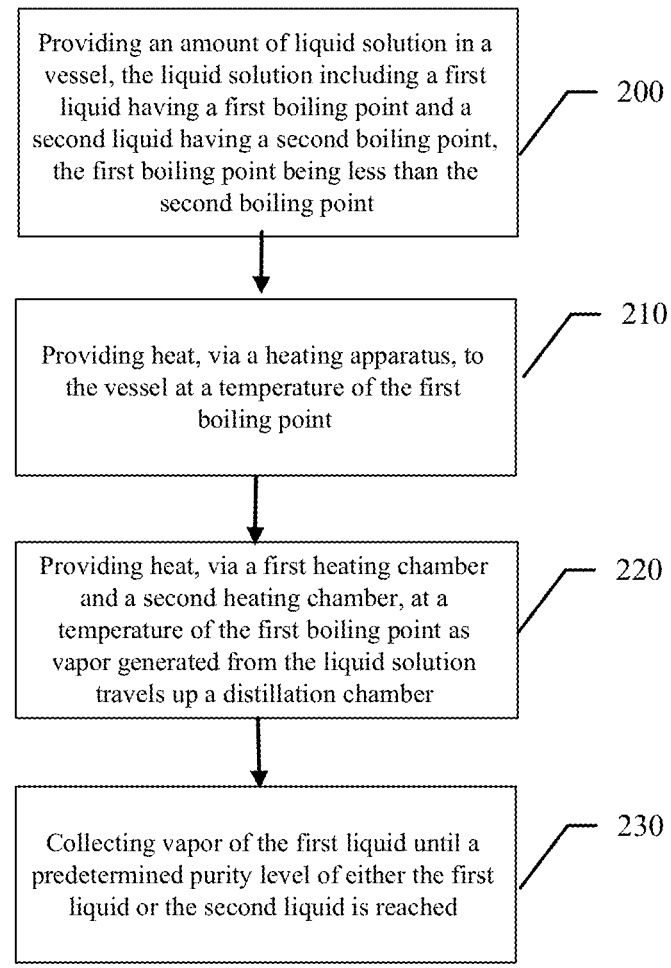
FIG. 6 illustrates a method of separating and purifying a liquid solution according to an example embodiment.

FIG. 6 illustrates a method of separating and purifying a liquid solution using the purification module 2 described herein. As shown in FIG. 6, the method may include providing an amount of liquid solution in a vessel, at operation 200. The liquid solution includes a first liquid having a first boiling point and a second liquid having a second boiling point, the first boiling point being lower than the second boiling point. At operation 210, the method also includes providing heat, via a heating apparatus, to the vessel at a temperature of the first boiling point. At operation 220, the method includes providing heat, via a first heating chamber and a second heating chamber, at a temperature of the first boiling point as vapor generated from the liquid solution travels up a distillation chamber. At operation 230, the method also includes collecting vapor of the first liquid until a predetermined purity level of either the first liquid or the second liquid is reached.

Example embodiments may therefore provide a purification module configured to separate and purify a liquid solution. The purification module may include a vessel configured to receive a predetermined amount of a liquid solution. The liquid solution may include a first liquid having a first boiling point and a second liquid having a second boiling point, and the first boiling point may be lower than the second boiling point. The purification module may also include a heating apparatus configured to apply heat to the vessel at a temperature of the first boiling point, and a column apparatus configured to separate the liquid solution into the first liquid and the second liquid and purify the first liquid and the second liquid to a determined purity level. The column apparatus may include a first heating chamber, a second heating chamber, and a distillation chamber. The distillation chamber may be located between the first heating chamber and the second heating chamber. The first heating chamber and second heating chamber may be configured to receive a heat transfer liquid to apply heat to the distillation chamber at the temperature of the first boiling point in order to enable separation and purification of the first liquid and the second liquid in the distillation chamber.

In some embodiments, the features described above may be augmented or modified, or additional features may be added. These augmentations, modifications and additions may be optional and may be provided in any combination. Thus, although some example modifications, augmentations and additions are listed below, it should be appreciated that any of the modifications, augmentations and additions could be implemented individually or in combination with one or more, or even all of the other modifications, augmentations and additions that are listed. As such, for example, the purification module may include a collection container configured to receive the first liquid when separated from the second liquid. Alternatively or additionally, the collection container may include a purity sensor configured to monitor a purity level of the first liquid collected in the collection container. Alternatively or additionally, the first heating chamber and the second heating chamber may extend along a longitudinal length of the distillation chamber. Alternatively or additionally, a wall of the first heating chamber may define an inner wall of the distillation chamber, and a wall of the second heating chamber may define an outer wall of the distillation chamber. Alternatively or additionally, each of the first heating chamber and the second heating chamber may include a temperature sensor configured to monitor the temperature of the heat transfer fluid circulating therein. Alternatively or additionally, the column apparatus may include a plurality of condensation structures, each of the plurality of condensation structures being disposed in an interior of the distillation chamber at a predefined distance from an end of the distillation chamber. Alternatively or additionally, each of the plurality of condensation structures may be formed from metal configured to conduct heat, and the heat transfer fluid of the first heating chamber and the second heating chamber may be configured to heat the plurality of condensation structures.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A purification module configured to separate and purify a liquid solution, the purification module comprising:
    a vessel configured to receive a liquid solution, the liquid solution comprising a first liquid having a first boiling point and a second liquid having a second boiling point, wherein the first boiling point is lower than the second boiling point;
    a heating apparatus operatively connected to the vessel; and
    a column apparatus configured to separate the liquid solution into the first liquid and the second liquid and purify the first liquid and the second liquid to a determined purity level, the column apparatus comprising:
        a first heating chamber,
        a second heating chamber, and
        a distillation chamber, the distillation chamber being located between the first heating chamber and the second heating chamber, and wherein a wall of the first heating chamber defines an inner wall of the distillation chamber, and a wall of the second heating chamber defines an outer wall of the distillation chamber;
    wherein the first heating chamber and second heating chamber are configured to receive a heat transfer liquid to apply heat to the distillation chamber at the temperature of the first boiling point in order to enable separation and purification of the first liquid and the second liquid in the distillation chamber.

2. The purification module of claim 1, wherein the purification module further comprises a collection container configured to receive the first liquid when separated from the second liquid.

3. The purification module of claim 2, wherein the collection container comprises a purity sensor configured to monitor a purity level of the first liquid collected in the collection container.

4. The purification module of claim 1, wherein the first heating chamber and the second heating chamber extend along a longitudinal length of the distillation chamber.

5. The purification module of claim 1, wherein each of the first heating chamber and the second heating chamber comprises a temperature sensor configured to monitor the temperature of the heat transfer fluid circulating therein.

6. The purification module of claim 1, wherein the column apparatus further comprises a plurality of condensation structures having surfaces on which a vapor of the second liquid condenses, each of the plurality of condensation structures being disposed in an interior of the distillation chamber at a predefined distance from an end of the distillation chamber.

7. The purification module of claim 6, wherein each of the plurality of condensation structures are formed from metal configured to conduct heat, wherein the heat transfer fluid of the first heating chamber and the second heating chamber is configured to heat the plurality of condensation structures.

8. A column apparatus configured to separate and purify a liquid solution, the liquid solution comprising a first liquid having a first boiling point and a second liquid having a second boiling point, the column apparatus comprising:
    a first heating chamber,
    a second heating chamber, and
    a distillation chamber, the distillation chamber being located between the first heating chamber and the second heating chamber, and wherein a wall of the first heating chamber defines an inner wall of the distillation chamber, and a wall of the second heating chamber defines an outer wall of the distillation chamber;
    wherein the first heating chamber and second heating chamber are configured to receive a heat transfer liquid to apply heat to the distillation chamber at the temperature of the first boiling point in order to enable separation and purification of the first liquid and the second liquid in the distillation chamber, wherein the first boiling point is lower than the second boiling point.

9. The column apparatus of claim 8, wherein the first heating chamber and the second heating chamber extend along a longitudinal length of the distillation chamber.

10. The column apparatus of claim 8, wherein each of the first heating chamber and the second heating chamber comprises a temperature sensor configured to monitor the temperature of the heat transfer fluid circulating therein.

11. The column apparatus of claim 8, wherein the column apparatus further comprises a plurality of condensation structures having surfaces on which a vapor of the second liquid condenses, each of the plurality of condensation structures being disposed in an interior of the distillation chamber at a predefined distance from an end of the distillation chamber.

12. The column apparatus of claim 11, wherein each of the plurality of condensation structures are formed from metal configured to conduct heat, wherein the heat transfer fluid of the first heating chamber and the second heating chamber is configured to heat the plurality of condensation structures.

13. The column apparatus of claim 11, wherein each of the plurality of condensation structures extend between and in contact with an inner wall and an outer wall of the distillation chamber in order to be heated by the heat transfer fluid of the first heating chamber and the second heating chamber.

14. A method of separating and purifying a liquid solution, the liquid solution comprising a first liquid having a first boiling point and a second liquid having a second boiling point, the first boiling point being lower than the second boiling point, the method comprising:
    providing an amount of the liquid solution in a vessel;
    applying heat to the vessel at a temperature of the first boiling point,
    applying heat, via a heat transfer fluid in a first heating chamber and a second heating chamber, to a distillation chamber at the temperature of the first boiling point as vapor generated from the liquid solution travels up the distillation chamber,
    maintaining a uniform temperature within the distillation chamber along an entire longitudinal length of the distillation chamber; and
    collecting and cooling the vapor of the first liquid until a predetermined purity level is reached.

15. The method of claim 14, wherein the method further comprises monitoring the temperature of the heat transfer fluid in the first heating chamber and the second heating chamber.

16. The method of claim 15, wherein response to the temperature of the heat transfer fluid in the first heating chamber or the second heating chamber falling below the first boiling point, increasing a flow rate of the heat transfer fluid circulating in a respective one of the first heating chamber or the second heating chamber.

17. The method of claim 15, wherein in response to the temperature of the heat transfer fluid in the first heating chamber or the second heating chamber rising above the first boiling point, decreasing the flow rate of the heat transfer fluid circulating in the respective one of the first heating chamber or the second heating chamber.

18. The method claim 14, wherein the method further comprises collecting condensed vapor of the second liquid in the vessel until the predetermined purity level is reached.

19. The method of claim 14, wherein the distillation chamber is located between the first heating chamber and the second heating chamber, and wherein a wall of the first heating chamber defines an inner wall of the distillation chamber, and a wall of the second heating chamber defines an outer wall of the distillation chamber.

* * * * *

UNITED STATES PATENT AND TRADEMARK OFFICE
CERTIFICATE OF CORRECTION

Page 1 of 1

PATENT NO. : 11,045,742 B2
APPLICATION NO. : 16/692058
DATED : June 29, 2021
INVENTOR(S) : Chris Wunz et al.

It is certified that error appears in the above-identified patent and that said Letters Patent is hereby corrected as shown below:

In the Claims

In Claim 16, Column 12, Line 39, "The method of claim 15, wherein response to the" should read -- The method of claim 15, wherein in response to the --.

In Claim 18, Column 12, Line 52, "The method claim 14, wherein the method further" should read -- The method of claim 14, wherein the method further --.

Signed and Sealed this
Eighth Day of March, 2022

Drew Hirshfeld
*Performing the Functions and Duties of the
Under Secretary of Commerce for Intellectual Property and
Director of the United States Patent and Trademark Office*